US011376268B2

(12) United States Patent
Badley

(10) Patent No.: US 11,376,268 B2
(45) Date of Patent: *Jul. 5, 2022

(54) METHODS AND MATERIALS FOR TREATING HUMAN IMMUNODEFICIENCY VIRUS INFECTIONS

(71) Applicant: Mayo Foundation for Medical Education and Research, Rochester, MN (US)

(72) Inventor: Andrew Badley, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 31 days.

This patent is subject to a terminal disclaimer.

(21) Appl. No.: 17/003,818

(22) Filed: Aug. 26, 2020

(65) Prior Publication Data

US 2020/0390789 A1 Dec. 17, 2020

Related U.S. Application Data

(63) Continuation of application No. 15/552,636, filed as application No. PCT/US2016/018776 on Feb. 19, 2016, now Pat. No. 10,786,519.

(60) Provisional application No. 62/119,318, filed on Feb. 23, 2015.

(51) Int. Cl.

| | | |
|---|---|---|
| A61K 31/69 | (2006.01) |
| A61K 39/00 | (2006.01) |
| A61K 31/513 | (2006.01) |
| A61K 31/675 | (2006.01) |
| A61K 38/20 | (2006.01) |
| A61K 31/635 | (2006.01) |
| A61K 39/21 | (2006.01) |
| A61K 31/505 | (2006.01) |
| A61K 38/05 | (2006.01) |
| A61K 31/4402 | (2006.01) |
| A61K 45/06 | (2006.01) |
| A61K 31/5365 | (2006.01) |

(52) U.S. Cl.
CPC .......... *A61K 31/69* (2013.01); *A61K 31/4402* (2013.01); *A61K 31/505* (2013.01); *A61K 31/513* (2013.01); *A61K 31/5365* (2013.01); *A61K 31/635* (2013.01); *A61K 31/675* (2013.01); *A61K 38/05* (2013.01); *A61K 38/2013* (2013.01); *A61K 38/2086* (2013.01); *A61K 39/21* (2013.01); *A61K 45/06* (2013.01)

(58) Field of Classification Search
CPC ................ A61K 38/2013; A61K 39/21; A61K 2300/00; A61K 45/06; A61K 31/337; A61K 31/437; A61K 47/545; A61K 47/6803; A61P 31/18; A61P 37/04; A61P 35/00; A61P 25/02

See application file for complete search history.

(56) References Cited

U.S. PATENT DOCUMENTS

| | | |
|---|---|---|
| 6,548,536 B2 | 4/2003 | Hara et al. |
| 2002/0091073 A1 | 7/2002 | Finkel et al. |
| 2003/0232738 A1 | 12/2003 | Finkel |
| 2009/0010941 A1 | 1/2009 | Stevenson et al. |
| 2010/0168004 A1 | 7/2010 | Williams et al. |
| 2014/0256705 A1 | 9/2014 | Hasvold et al. |
| 2014/0309289 A1 | 10/2014 | Anderson |
| 2018/0036322 A1 | 2/2018 | Badley |
| 2018/0161347 A1 | 6/2018 | Badley et al. |

FOREIGN PATENT DOCUMENTS

| | | |
|---|---|---|
| WO | WO 2000/033654 | 6/2000 |
| WO | WO 2006/017346 | 2/2006 |
| WO | WO 2006/023778 | 3/2006 |
| WO | WO 2009/036051 | 3/2009 |
| WO | WO 2011/089166 | 7/2011 |
| WO | WO 2011/089167 | 7/2011 |

OTHER PUBLICATIONS

Adams et al., "Potent and selective inhibitors of the proteasome: dipeptidyl boronic acids," Bioorg Med Chem lett., 8(4):333-338, Feb. 17, 1998.
Adams et al., "Proteasome inhibitors: a novel class of potent and effective antitumor agents," Cancer Res., 59(11):2615-2622, Jun. 1, 1999.
Adams, "Development of the proteasome inhibitor PS-341," Oncologist., 7(1):9-16, 2002.
Adams, "Proteasome inhibition in cancer: development of PS-341," Semin Oncol., 28(6):613-619, Dec. 2001.
An et al., "Protease inhibitor-induced apoptosis: accumulation of wt p53, p21WAF1/CIP1, and induction of apoptosis are independent markers of proteasome inhibition," Leukemia., 14(7):1276-1283, Jul. 2000.
Archin et al., "Administration of vorinostat disrupts HIV-1 latency in patients on antiretroviral therapy," Nature., 487(7408):482-485, Jul. 25, 2012.
Archin et al., "Antiretroviral intensification and valproic acid lack sustained effect on residual HIV-1 viremia or resting CD4+ cell infection," Plos One., 5(2):e9390, Feb. 2010, 4 pages.
Archin et al., "Expression of latent HIV induced by the potent HDAC inhibitor suberoylanilide hydroxamic acid," AIDS Res Hum Retroviruses., 25(2):207-212, Feb. 2009.
Arkin et al., "Small-Molecule Inhibitors of Protein-Protein Interactions: Progressing toward the Reality," Chem Biol., 21(9):1102-1114, 2014.
Badley, "Altering cell death pathways as an approach to cure HIV infection," Cell Death and Dis., 4:e718, Jul. 2013.

(Continued)

*Primary Examiner* — Bao Q Li
(74) *Attorney, Agent, or Firm* — Fish & Richardson P.C.

(57) ABSTRACT

This document provides methods and materials for treating HIV infections. For example, methods and materials for using one or more proteosome inhibitors in combination with one or more other agents to treat HIV infections are provided.

8 Claims, 13 Drawing Sheets

(56) References Cited

OTHER PUBLICATIONS

Balazs et al., "Antibody-based protection against HIV infection by vectored immunoprophylaxis," Nature., 481(7379):81-84, Nov. 30, 2011.
Bullen et al., "New ex vivo approaches distinguish effective and ineffective single agents for reversing HIV-1 latency in vivo," Nat Med., 20(4):425-429, Apr. 2014.
Caselli et al., "Short Communication: Activating Transcription Factor 4 (ATF4) Promotes HIV Type 1 Activation," AIDS Res Hum Retroviruses., 28(8):907-912, Aug. 2012.
Choudhary et al., "MCL-1 and BCL-xL-dependent resistance to the BCL-2 inhibitor ABT-199 can be overcome by preventing PI3K/AKT/mTOR activation in lymphoid malignancies," Cell death & disease, 6(1):e1593, Jan. 2015.
Chun, T.-W., et al., Jun. 2015, HIV reservoirs as obstacles and opportunities for an HIV cure, Nat. Innnnunol. 16(6):584-589.
Cooper et al., "HIV-1 causes CD4 cell death through DNA-dependent protein kinase during viral integration," Nature., 498:376-379, Jun. 20, 2013.
Coull et al., "The Human Factors YY1 and LSF Repress the Human Immunodeficiency Virus Type 1 Long Terminal Repeat via Recruitment of Histone Deacetylase 1," J Virol., 74(15):6790-6799, Aug. 2000.
Cummins et al., "Maintenance of the HIV reservoir is antagonized by selective BCL2 inhibition," J Virol,, 91(11):e00012-17, Jun. 2017.
Cummins et al., ""Prime, shock, and kill: priming CD4 T cells from HIV patients with a BCL-2 antagonist before HIV reactivation reduces HIV reservoir size,"" J Virol., 90(8):4032-4048, Apr. 2016.
Dai et al., "Proteasome inhibitors potentiate leukemic cell apoptosis induced by the cyclin-dependent kinase inhibitor flavopiridol through a SAPK/JNK- and NF-kappaB-dependent process," Oncogene., 22(46):7108-7122, Oct. 16, 2003.
Deeks and Walker., "Human immunodeficiency virus controllers: mechanisms of durable virus control in the absence of antiretroviral therapy," Immunity., 27:406-416, Sep. 2007.
Deeks et al., "The end of AIDS: HIV infection as a chronic disease," Lancet., 382(9903):1525-1533, Nov. 2, 2013.
Deeks, S. G., et al., Aug. 2016, International AIDS Society global scientific strategy: towards an HIV cure 2016, Nat. Med. 22(8): 839-850.
Deeks., "Towards an HIV cure: a global scientific strategy," Nature Reviews Immunology,, 12:607-614, Jul. 2012.
Doitsh et al., "Abortive HIV infection mediates CD4 T cell depletion and inflammation in human lymphoid tissue," Cell., 143(5):789-801, Nov. 24, 2010.
Dowlatshahi et al., "ALIX is a Lys63-Specific Polyubiquitin Binding Protein that Functions in Retrovirus Budding," Dev Cell., 23(6):1247-1254, Dec. 11, 2012.
Extended European Search Report in European Application No. 16756096.0, dated Dec. 11, 2018, 245 pages.
Extended European Search Report in European Application No. 16783754.1 dated Oct. 17, 2018, 22 pages.
Fauci et al., "An HIV Cure: Feasibility, Discovery, and Implementation," JAMA., 312(4):335-336, Jul. 23-30, 2014.
Fernandez et al., "Differential Regulation of Noxa in Normal Melanocytes and Melanoma Cells by Proteasome Inhibition: Therapeutic Implications," Cancer Res., 65(14):6294-6304, Jul. 15, 2005.
Finzi et al., "Latent infection of CD4+ T cells provides a mechanism for lifelong persistence of HIV-1, even in patients on effective combination therapy," Nat Med., 5(5):512-517, May 1999.
Henrich et al., "Long-term reduction in peripheral blood HIV type 1 reservoirs following reduced-intensity conditioning allogeneic stem cell transplantation," J Infect Dis., 207(11):1694-1702, Jun. 1, 2013.
Hideshima et al., "The proteasome inhibitor PS-341 inhibits growth, induces apoptosis, and overcomes drug resistance in human multiple myeloma cells," Cancer Res., 61(7):3071-3076, Apr. 1, 2001.

Holt et al., "Human hematopoietic stem/progenitor cells modified by zinc-finger nucleases targeted to CCR5 control HIV-1 in vivo," Nature Biotech., 28(8):839-847, Aug. 2010.
Hutter et al., "Long-Term Control of HIV by CCR5 Delta32/Delta32 Stem-Cell Transplantation," N Engl. J Med., 360:692-698, Feb. 12, 2009.
International Preliminary Report on Patentability in International Application No. PCT/US2016/018776, dated Sep. 8, 2017, 7 pages.
International Preliminary Report on Patentability of International Application No. PCT/US2016/028419, dated Oct. 24, 2017.
International Search Report and Written Opinion in the International Application No. PCT/US2016/18776, dated Apr. 29, 2016, 9 pages.
International Search Report and Written Opinion of International Application No. PCT/US2016/28419, dated Aug. 15, 2016, 9 pages.
Jostins et al., "Host-microbe interactions have shaped the genetic architecture of inflammatory bowel disease," Nature., 491(7422):119-124, Nov. 1, 2012.
Keedy et al., "A limited group of class I histone deacetylases acts to repress human immunodeficiency virus type 1 expression," J Virol., 83(10):4749-4756, May 2009.
Kikuchi et al., "Histone deacetylases are critical targets of bortezomib-induced cytotoxicity in multiple myeloma," Blood., 116(3):406-417, 2010.
Kitchen et al., "In vivo suppression of HIV by antigen specific T cells derived from engineered hematopoietic stem cells," PLOS Pathog., 8(4):e1002649, Apr. 2012.
Kumar et al., "Safety and tolerability of ixazomib, an oral proteasome inhibitor, in combination with lenalidomide and dexamethasone in patients with previously untreated multiple myeloma: an open-label phase 1/2 study," Lancet., 14:1503-1512, Dec. 2014.
Lam et al., "Switching virally suppressed, treatment-experienced patients to a raltegravir-containing regimen does not alter levels of HIV-1 DNA," PLOS ONE., 7(3):e31990, 2012.
Ling et al., "PS-341, a novel proteasome inhibitor, induces Bcl-2 phosphorylation and cleavage in association with G2-M phase arrest and apoptosis," Mol Cancer Ther., 1(10):841-849, Aug. 2002.
Liu et al., "Influence of Primate Lentiviral Vif and Proteasome Inhibitors on Human Immunodeficiency Virus Type 1 Virion Packaging of APOBEC3G," J Virol., 78(4):2072-2081, Feb. 2004.
Marban et al., "Recruitment of chromatin-modifying enzymes by CTIP2 promotes HIV-1 transcriptional silencing," EMBO J., 26(2):412-423, 2007.
Margolis, D. M., et al., Jul. 2016, Latency reversal and viral clearance to cure HIV-1, Science 353(6297): aaf6517/1-7.
Mateos et al., "Maintenance therapy with bortezomib plus thalidomide or bortezomib plus prednisone in elderly multiple myeloma patients included in the GEM2005MAS65 trial," Blood., 120(13) 2581-2588, 2012.
Mbita et al., "Human Immunodeficiency Virus-1 (HIV-1)-Mediated Apoptosis; New Therapeutic Targets," Viruses., 6(8):3181-3227, 2014.
Miller et al. Proteasonne inhibitors act as bifunctional antagonists of human immunodeficiency virus type 1 latency and replication. Retrovirology 2013, 10:120: 1-15.
Mitsiades et al., "Molecular sequelae of proteasome inhibition in human multiple myeloma cells," PNAS USA., 99(22):14374-14379, Oct. 29, 2002.
Mitsiades et al., "The proteasome inhibitor PS-341 potentiates sensitivity of multiple myeloma cells to conventional chemotherapeutic agents: therapeutic applications," Blood., 101(6):2377-2380, Mar. 15, 2003.
Moreau et al. "Oral therapy for multiple myeloma: ixazomib arriving soon" Blood., 2014; 124(7): 986-987.
Moreau et al., "Subcutaneous versus intravenous administration of bortezomib in patients with relapsed multiple myeloma: a randomised, phase 3, non-inferiority study," Lancet Oncol., 12(5):431-40, May 2011.
Natesampillai et al., "The proapoptotic, HIV protease generated Casp8p41 when bound and inactivated by Bcl 1, is degraded by the proteasome," J Virol., Posted Online Apr. 11, 2018, Retrieved Aug. 15, 2018, Retrieved from Internet: URL <http://jvi.asm.org/>, 40 pages.
Nie et al., "Human immunodeficiency virus type 1 protease cleaves procaspase 8 in vivo," J Virol., 81(13):6947-6956, Jul. 2007.

(56) References Cited

OTHER PUBLICATIONS

Obeng et al., "Proteasome inhibitors induce a terminal unfolded protein response in multiple myeloma cells," Blood., 107(12):4907-4916, Jun. 15, 2006.
Offidani et al., "An evidence-based review of ixazomib citrate and its potential in the treatment of newly diagnosed multiple myeloma," OncoTargets Ther., 7:1793-1800, Sep. 29, 2014.
Petrovas et al., "HIV-specific CD8+ T cells exhibit markedly reduced levels of Bcl-2 and Bcl-xL," J Immunol., 172(7):4444-4453, 2004.
Pham et al., "Global burden of transmitted HIV drug resistance and HIV-exposure categories: a systematic review and meta-analysis," AIDS., 28(18):2751-2762, Nov. 28, 2014.
Qin et al., "Proteasome Inhibitors Trigger NOXA-Mediated Apoptosis in Melanoma and Myeloma Cells," Cancer Res., 65(14):6282-6293, Jul. 15, 2005.
Rerks-Ngarm et al., "Vaccination with ALVAC and AIDSVAX to prevent HIV-1 Infection in Thailand," NEJM., 361(23):2209-2220, Dec. 3, 2009.
Richman et al., "The challenge of finding a cure for HIV infection," Science., 323(5919):1304-1307, Mar. 6, 2009.
Saleh et al., "CCR7 ligands CCL19 and CCL21 increase permissiveness of resting memory CD4+ T cells to HIV-1 infection: a novel model of HIV-1 latency," Blood., 110(13):4161-4164, Dec. 15, 2007.
Sandstrom et al., "bcl-2 Expression Facilitates Human Immunodeficiency Virus Type 1-Mediated Cytopathic Effects during Acute Spreading Infections," J Virol., 70(7):4617-4622, 1996.
Savarino et al., "Shock and kill effects of class I-selective histone deacetylase inhibitors in combination with the glutathione synthesis inhibitor buthionine sulfoximine in cell line models for HIV-1 quiescence," Retrovirology., 6:52, 2009.
Scholler et al., "Decade-long safety and function of retroviral-modified chimeric antigen receptor T cells," Sci Transl Med., 4(132):132ra53, May 2, 2012.
Shah et al., "26S proteasome inhibition induces apoptosis and limits growth of human pancreatic cancer," J Cell Biochem., 82(1):110-122, Apr. 2-27, 2001.
Shan and Silicaiano from reactivation of latent HIV-1 to elimination of the latent reservoir: The presence of multiple barriers to viral eradication. Bioessays, 2013; 35: 544-552.
Shan et al., "Stimulation of HIV-1-specific cytolytic T lymphocytes facilitates elimination of latent viral reservoir after virus reactivation," Immunity., 36(3):491-501, Mar. 23, 2012.
Shan et al., "Stimulation of HIV-1-specific cytolytic T lymphocytes facilitates elimination of latent viral reservoir after virus reactivation," Immunity., 36:491-501, Mar. 23, 2012.
Souers et al., "ABT-199, a potent and selective BCL-2 inhibitor, achieves antitumor activity while sparing platelets," Nat Med., 19(2):202-208, 2013.
Strack et al., "Apoptosis mediated by HIV protease is preceded by cleavage of Bcl-2," Proc Natl Acad Sci U S A., 93(18):9571-9576, Sep. 3, 1996.
Sunwoo et al., "Novel proteasome inhibitor PS-341 inhibits activation of nuclear factor-kappa B, cell survival, tumor growth, and angiogenesis in squamous cell carcinoma," Clin Cancer Res., 7(5):1419-1428, May 2001.
Tebas et al., "Gene editing of CCR5 in autologous CD4 T cells of persons infected with HIV," NEJM., 370(10):901-910, Mar. 6, 2014.
Teicher et al., "The proteasome inhibitor PS-341 in cancer therapy," Clin Cancer Res., 5(9):2638-2645, Sep. 1999.
Tsai et al., "Retro-translocation of proteins from the endoplasmic reticulum into the cytosol," Nat Rev Mol Cell Biol., 3(4):246-255, Apr. 1, 2002.
Turan et al., "Changes in protein profiles of multiple myeloma cells in response to bortezomib," Leuk Lymphoma., 54(5):1061-1068, May 2013.
Van Lint et al., "Transcriptional activation and chromatin remodeling of the HIV-1 promoter in response to histone acetylation," EMBO J., 15(5):1112-1120, Mar. 1, 1996.
Wang et al., "Molecules from apoptotic pathways modulate HIV-1 replication in Jurkat cells," Biochem Biophys Res Commun., 414(1):20-24, Oct. 14, 2011.
Warriner et al., "HIV-related metabolic comorbidities in the current ART era," Infect Dis Clin North Am., 28(3):457-476, Sep. 2014.
Wei et al., "MLN2238 synergizes BH3 mimetic ABT-263 in castration-resistant prostate cancer cells by induction of NOXA," Tumour Biol., 35(10):10213-10221., Oct. 2014.
Williams et al., "NF-κB p50 promotes HIV latency through HDAC recruitment and repression of transcriptional initiation," EMBO J., 25(1):139-149, Jan. 11, 2006.
Xing et al., "Disulfiram reactivates latent HIV-1 in a Bcl-2-transduced primary CD4+ T cell model without inducing global T cell activation," J. of Virology, 85(12):6060-4, Jun. 2011.
Xing, S., and R. F. Siliciano, Jun. 2013, Targeting HIV latency: pharmacologic strategies toward eradication, Drug Discov. Today 18(11/12):541-551.
Yu et al., "Proteasome inhibitors block HIV-1 replication by affecting both cellular and viral targets," Biochemical and Biophysical Research Communications., 385(1):100-105, Jul. 17, 2009.
Zhang et al., "Bcl-2 upregulation by HIV-1 Tat during infection of primary human macrophages in culture," J Biomed Sci., 9(2):133-139, Mar.-Apr. 2002.

METHODS AND MATERIALS FOR TREATING HUMAN IMMUNODEFICIENCY VIRUS INFECTIONS

CROSS REFERENCE TO RELATED APPLICATIONS

This application is a continuation of U.S. application Ser. No. 15/552,636, filed Aug. 22, 2017 know U.S. Pat. No. 10,786,519), which is a National Stage application under 35 U.S.C. § 371 of International Application No. PCT/US2016/018776, having an International Filing Date of Feb. 19, 2016, which claims the benefit of U.S. Provisional Ser. No. 62/119,318, filed Feb. 23, 2015. This disclosure of the prior applications are considered part of (and are incorporated by reference in) the disclosure of this application.

STATEMENT AS TO FEDERALLY SPONSORED RESEARCH

This inventor was made with government supposed under AI110173 awarded by the National Institutes of Health. The government has certain rights in the invention.

BACKGROUND

1. Technical Field

This document relates to methods and materials involved in treating human immunodeficiency virus (HIV) infections. For example, this document provides methods and materials for using one or more proteosome inhibitors in combination with one or more other agents to treat HIV infections.

2. Background Information

HIV is a retrovirus that causes the acquired immunodeficiency syndrome (AIDS), which is a medical condition where progressive failure of the immune system leads to life-threatening opportunistic infections. The HIV infection, while treatable for long periods of time, remains a largely incurable infection. On the other hand, an HIV infection was "cured" in one patient, which involved using myeloablative chemotherapy and maximally suppressive antiretroviral therapy (ART), followed by bone marrow transplantation (BMT; Hater et al., *N. Engl. J. Med.*, 360:692-698 (2009)).

SUMMARY

This document provides methods and materials for treating HIV infections. For example, this document provides methods and materials for using one or more proteosome inhibitors in combination with one or more other agents to treat HIV infections. An obstacle to curing an HIV infection is the existence of transcriptionally silent integrated HIV proviruses that reside in resting memory CD4 T cells, which are difficult to eliminate because they are resistant to the cytotoxic and pro-apoptotic effects of viral reactivation. The reasons that latently infected CD4 T cells resist the pro-death effects of intracellular HIV proteins are (i) memory CD4 T cells are apoptosis resistant, and (ii) chronic or latent HIV infection causes an apoptosis resistant phenotype. It is this apoptosis resistance that appears to be the reason that latently HIV infected cells do not die following viral reactivation, even though viral reactivation results in expression of pro-apoptotic factors (e.g., Env, Tat, Nef, protease and Vpr, and likely others factors such as FasL and TRAIL).

As described herein, altering the susceptibility of latently HIV infected cells (e.g., latently HIV infected CD4 T cells or resting memory CD4 T cells) that have become resistant to the pro-apoptotic effects of intracellular HIV replication, so that these cells become susceptible again to the pro-apoptotic effects of productive HIV replication can be used to treat HIV infections. ART drugs do not treat latently HIV infected cells. The only drugs that act on these latently HIV infected cells are latency reversing agents (LRAs), but LRAs do not cause latently HIV infected cells to die. Thus, the number of latently HIV infected cells can remain stable over time. As described herein, proteosome inhibitors alone such as bortezomib or ixazomib can induce HIV reactivation. Moreover, when HIV is reactivated in latently HIV infected cells (whether the HIV reactivation is induced by a proteosome inhibitor, another agent such as an LRA, or a condition such as an inflammatory reaction) in the presence of a proteosome inhibitor, those HIV reactivating cells die. Thus, in some cases, HIV infections can be treated by administering maximally suppressive ART to prevent or reduce the level of repopulation of the HIV reservoir and by administering one or more proteosome inhibitors such as bortezomib or ixazomib to render latently HIV infected cells susceptible to the cytotoxic effects of pro-apoptotic HIV proteins, to promote HIV reactivation (e.g., with a proteosome inhibitor or with an LRA), and to cause accumulation of HIV proteins within the infected cell (since proteasome inhibitors can prevent HIV budding and prevent proteasome mediated degradation of those proteins), altogether resulting in the intracellular expression of the pro-apoptotic HIV proteins such as Tat, Nef, Env, Vpr, and protease, which then can cause the death of those HIV reactivating cells that were latently infected with HIV.

In general, one aspect of this document features a method for reducing the number of latently HIV infected cells within a human infected with HIV. The method comprises, or consists essentially of, (a) administering a proteosome inhibitor to the human, and (b) administering a combination of anti-retroviral agents to the human. The cells can be CD4$^+$ T cells. The proteosome inhibitor can be ixazomib or bortezomib. The proteosome inhibitor can be ixazomib. The combination can comprise an integrase inhibitor, a protease inhibitor, and a reverse transcriptase inhibitor. The integrase inhibitor can be raltegravir. The protease inhibitor can be darunavir or atazanavir. The reverse transcriptase inhibitor can be selected from the group consisting of emtricitabine, rilpivirine, and tenofovir. The method can comprise administering a latency reversing agent to the human. The latency reversing agent can be selected from the group consisting of an HDAC inhibitor, a phorbol ester (e.g., prostratin), IL-2, and a bromodomain inhibitor. The method can comprise administering an immunotherapeutic agent, a vaccine, or a nucleic acid to the human. The method can comprise administering an immunotherapeutic agent to the human, wherein the immunotherapeutic agent is IL-15. The method can comprise administering a vaccine to the human. The method can comprise administering a nucleic acid to the human, wherein the nucleic acid is designed to reduce CCR5 polypeptide expression.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
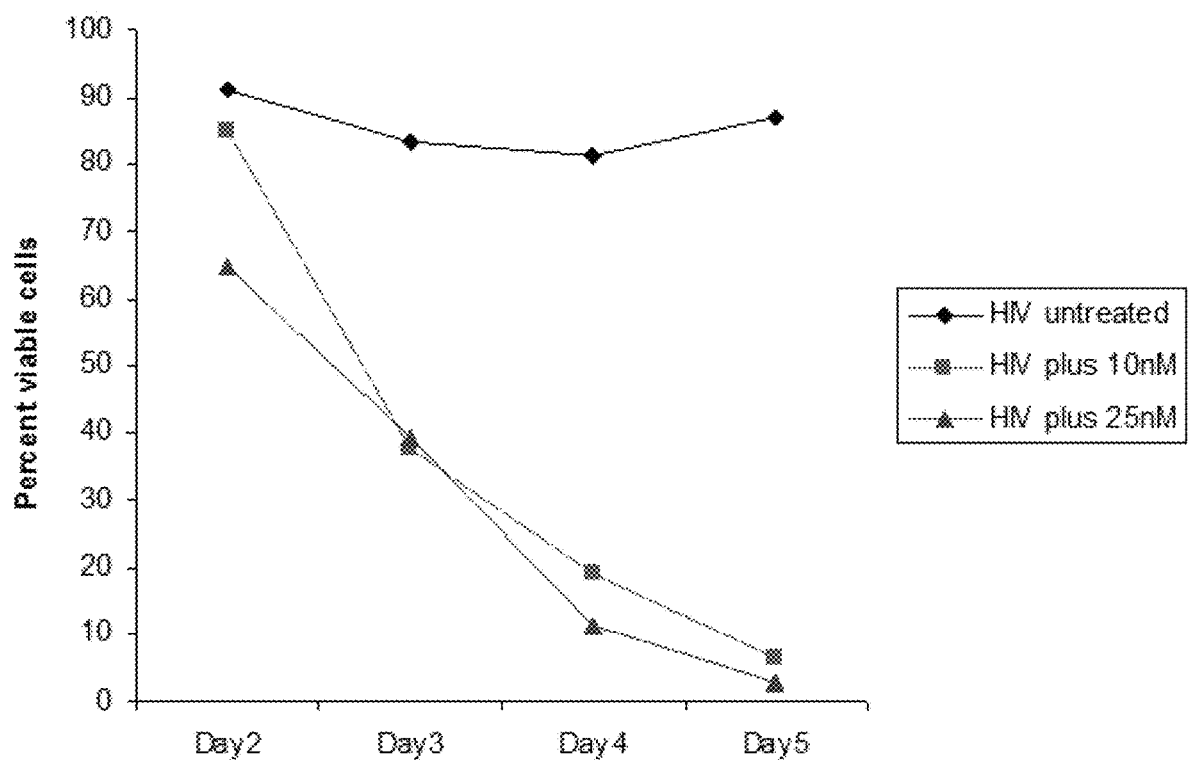
FIG. 1 is a graph plotting the percent of viable HIVIIIb infected Jurkat T cells that were untreated or treated (10 or 25 nM of bortezomib) for up to five days.

This document provides methods and materials for treating HIV infections. For example, this document provides methods and materials for using one or more proteosome inhibitors in combination with one or more other agents to treat HIV infections. In some cases, one or more proteosome inhibitors can be used to cause latently HIV infected cells to die following HIV reactivation in those latently HIV infected cells.

Any appropriate method can be used to identify a human having an HIV infection. For example, HIV blood tests can be used to identify a human having an HIV infection.

Once identified as having an HIV infection, the human can be administered ART (e.g., maximally suppressive ART) to prevent or reduce the level of repopulation of the HIV reservoir and one or more proteosome inhibitors to increase the susceptibility of latently HIV infected cells to cell death upon HIV reactivation, to induce HIV reactivation of latently HIV infected cells, and/or to cause accumulation of HIV proteins within the reactivating cells, all of which can synergize to cause the death of HIV infected cells.

An ART can include any appropriate anti-retroviral agent or combination of anti-retroviral agents. Examples of anti-retroviral agents that can be used for ART include, without limitation, HIV integrase inhibitors, HIV protease inhibitors, and reverse transcriptase inhibitors. Examples of ITV integrase inhibitors include, without limitation, raltegravir (also known as Isentress or MK-0518), dolutegravir, and elvitegravir. Examples of HIV protease inhibitors include, without limitation, lopinavir and atazanavir. Examples of reverse transcriptase inhibitors include, without limitation, emtricitabine, rilpivirine, and tenofovir. In some cases, combinations of anti-retroviral agents can be formulated into a single dosage form (e.g., a single pill or capsule) such as Complera® (emtricitabine, rilpivirine, and tenofovir), Atripla® (efavirenz, emtricitabine, and tenofovir DF), Stribild® (cobicistat, elvitegravir, emtricitabine, and tenofovir), and Triumeq® (abacavir, dolutegravir, and lamivudine).

Any appropriate proteosome inhibitor or combination of proteosome inhibitors (e.g., a combination of two, three, four, five, or more different proteosome inhibitors) can be used as described herein. Examples of proteosome inhibitors that can be used as described herein include, without limitation, bortezomib (N-pyrazinecarbonyl-L-phenylalanine-L- leucine boronic acid; Velcade®; Millennium Pharmaceuticals), ixazomib (4-(carboxymethyl)-2-((R)-1-(2-(2,5-dichlorobenzamido)acetamido)-3-methylbutyl)-6-oxo-1,3,2-dioxaborinane-4-carboxylic acid, Millennium Pharmaceuticals), and carfilzomib ((S)-4-Methyl-N-((S)-1-4(S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide; Kyprolis®, Onyx Pharmaceuticals, Inc.).

In some cases, one or more proteosome inhibitors can be formulated into a pharmaceutically acceptable composition for administration to a human having an HIV infection. For example, a therapeutically effective amount of bortezomib or ixazomib can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules. A pharmaceutical composition containing one or more proteosome inhibitors can be designed for oral or parenteral (including subcutaneous, intramuscular, intravenous, and intradermal) administration. When being administered orally, a pharmaceutical composition containing one or more proteosome inhibitors can be in the form of a pill, tablet, or capsule. Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

In some cases, a pharmaceutically acceptable composition including one or more proteosome inhibitors can be administered systemically. For example, a composition containing a proteosome inhibitor can be administered systemically orally or by injection to a human.

Effective doses can vary depending the route of administration, the age and general health condition of the human, excipient usage, the possibility of co-usage with other therapeutic treatments such as use of anti-retroviral agents and/or latency reversing agents, and the judgment of the treating physician.

An effective amount of a composition containing one or more proteosome inhibitors can be any amount that increases the susceptibility of latently HIV infected cells to cell death upon HIV reactivation, incudes HIV reactivation of latently HIV infected cells, or both increases the susceptibility of latently HIV infected cells to cell death upon HIV reactivation and induces HIV reactivation of latently HIV infected cells, thereby causing the latently HIV infected cells to die, without producing significant toxicity to the human. If a particular human fails to respond to a particular amount, then the amount of proteosome inhibitor can be increased by, for example, two fold. After receiving this higher amount, the human can be monitored for both responsiveness to the treatment and toxicity symptoms, and adjustments made accordingly. The effective amount can remain constant or can be adjusted as a sliding scale or variable dose depending on the human's response to treatment. Various factors can influence the actual effective amount used for a particular application. For example, the frequency of administration, duration of treatment, use of multiple treatment agents, route of administration, and severity of the HIV infection may require an increase or decrease in the actual effective amount administered.

The frequency of administration of a composition containing one or more proteosome inhibitors can be any frequency that increases the susceptibility of latently HIV infected cells to cell death upon HIV reactivation, incudes HIV reactivation of latently HIV infected cells, or both increases the susceptibility of latently HIV infected cells to cell death upon HIV reactivation and induces HIV reactivation of latently HIV infected cells, thereby causing the latently HIV infected cells to die, without producing significant toxicity to the human. For example, the frequency of administration can be from about daily to about once a week. The frequency of administration can remain constant or can be variable during the duration of treatment. As with the effective amount, various factors can influence the actual frequency of administration used for a particular application. For example, the effective amount, duration of treatment, use of multiple treatment agents, route of administration, and severity of the HIV infection may require an increase or decrease in administration frequency.

An effective duration for administering a composition containing one or more proteosome inhibitors can be any duration that increases the susceptibility of latently HIV infected cells to cell death upon HIV reactivation, incudes HIV reactivation of latently HIV infected cells, or both increases the susceptibility of latently HIV infected cells to cell death upon HIV reactivation and induces HIV reactivation of latently HIV infected cells, thereby causing the latently HIV infected cells to die, without producing significant toxicity to the human. Thus, the effective duration can vary from several months to several years. In general, the effective duration for the treatment of an HIV infection as described herein can range in duration from about two months to about five years. Multiple factors can influence the actual effective duration used for a particular treatment. For example, an effective duration can vary with the frequency of administration, effective amount, use of multiple treatment agents, route of administration, and severity of the HIV infection being treated.

In some cases, a human having an HIV infection can be treated with one or more proteosome inhibitors as described herein in combination with (a) one or more anti-retroviral agents, (b) one or more latency reversing agents, (c) one or more immunotherapeutic agents, (d) one or more vaccines (e.g., a vaccine formulated for assisting in the treatment of an HIV infection), (e) one or more nucleic acid-based therapies, (f) one or more chimeric TRIMS a polypeptides designed to restrict HIV expression, and (g) one or more advanced (e.g., third or later generation) chimeric antigen receptors expressed on CD8 T cells or NK cells designed to generate anti-HIV immunity. Examples of latency reversing agents that can be used in combination with one or more proteosome inhibitors as described herein include, without limitation, HDAC inhibitors, phorbol esters, IL-2, bromodomain inhibitors, and those described elsewhere (Bullen et al., *Nature Medicine*, 20:425-429 (2014)). Examples of HDAC inhibitors that can be used as latency reversing agents include, without limitation, vorinostat, panabinostat, and valproic acid. Examples of phorbol esters that can be used as latency reversing agents include, without limitation, prostratin and PMA. An example of a bromodomain inhibitor that can be used as a latency reversing agent includes, without limitation, JQ1 ((S)-tert-butyl 2-(4-(4-chlorophenyl)-2,3,9-trimethyl-6H-thieno[3,2-f][1,2,4]triazolo[4,3-a][1,4]diazepin-6-yl)acetate).

Examples of immunotherapeutic agents that can be used in combination with one or more proteosome inhibitors as described herein include, without limitation, IL-15, CD4 immunotoxin, and neutralizing anti-HIV antibodies. For example, a human having an HIV infection can be administered one or more proteosome inhibitors as described herein and IL-15.

Examples of vaccines that can be used in combination with one or more proteosome inhibitors as described herein include, without limitation, HIV tat or env antigens delivered by any number of platforms including genetic immunization, viral or virus like particle delivery, or delivery as recombinant proteins. The HIV antigens can be delivered with adjuvants such as CPG or GM-CSF. In some cases, a human having an HIV infection can be administered one or more proteosome inhibitors as described herein and a HIV tat or env vaccine.

Examples of nucleic acid-based therapies that can be used in combination with one or more proteosome inhibitors as described herein include, without limitation, nucleic acid molecules having the ability to reduce CCR5 polypeptide expression (e.g., siRNA molecules designed to reduce CCR5 polypeptide expression) and TALEN or CRISPR/Cas constructs designed to excise HIV DNA. For example, a human having an HIV infection can be administered one or more proteosome inhibitors as described herein and an siRNA molecule designed to reduce CCr5 polypeptide expression.

In some cases, a human having an HIV infection can be treated with one or more proteosome inhibitors as described herein in combination with one or more anti-retroviral agents plus any one or more of (a) one or more latency reversing agents, (b) one or more immunotherapeutic agents, (c) one or more vaccines (e.g., a vaccine formulated for assisting in the treatment of an HIV infection), and (d) one or more nucleic acid-based therapies.

In some cases, the level of HIV infected cells within a human being treated can be monitored during the course of treatment. Any appropriate method can be used to determine the level of HIV infected cells within a human. For example, the level of HIV infected cells within a human can be assessed using PCR based detection methods (nested or un-nested) for detecting HIV DNA, quantitative viral outgrowth assays (QVOA) for measuring replication competent HIV levels, or TILDA (Tat/rev; Induced Limiting Dilution Assay) that can measure the frequency of cells with multiply spliced HIV RNA as a surrogate for replication competent HIV.

The invention will be further described in the following examples, which do not limit the scope of the invention described in the claims.

EXAMPLES

Example 1

Using Proteosome Inhibitors to Cause Latently HIV Infected Cells to Die Following HIV Reactivation HIV infection is effectively treated by a number of antiretroviral medication, which when used in well proven combinations effectively suppress HIV replication, and persons on these treatments no longer experience life threatening immunosuppression associated with HIV infection. Even though combination antiretroviral therapy reverses the immunodeficiency of HIV, it does not normalize health of infected individuals. For example, treated HIV patients experience accelerated rates of diseases associated with ageing, likely as a consequence of on-going inflammation, including stroke, heart disease, diabetes, and osteoporosis (Warriner et al., *Infect. Dis. Clin. North Am.*, 28(3):457-76 (2014)).

A principal obstacle to curing an HIV infection is the existence of a long lived population of resting memory CD4 T cells, in which HIV has integrated into the host genome, where it lays dormant, and thus does not express any HIV proteins. Thus, current antiretroviral agents, which target HIV encoded proteins do not target these cells, nor do anti-HIV specific immune response as no target antigen is expressed. Current ART does, however, efficiently control and reduce HIV replication (reflected by HIV plasma RNA levels) to undetectable levels, such that in a well-treated patient, the majority of HIV persists in the latent (integrated DNA) state. The quiescent nature of this reservoir is associated with a long half-life of latently HIV infected CD4 T cells (estimated at about 44 months), such that a predicted 70 years of therapy would be required to cure HIV assuming that no HIV reactivation would occur during that time frame. Of course, however HIV reactivates with concomitant inflammation for example during "colds" or with vaccinations, and these viral "blips" serve to repopulate the HIV reservoir. Thus, the size of the HIV reservoir can be remarkable stable over years, and to date there have been no interventions identified which reliably reduce the size of the HIV reservoir. Importantly, when HIV reactivates from latency, those reactivating cells do not die. As described herein, when latently HIV infected cells are treated with proteasome inhibitors, those cells which reactivate HIV die, whereas cells which do not contain HIV are spared.

Latently infected CD4 T cells are rare in HIV infected and treated individuals, being present at a frequency of about 1 per million CD4 T cells. Moreover, as HIV is latent, there are no cell surface markers that can be used to identify latently infected cells. Thus, isolation, purification, and study of these cells using ex vivo samples is practically impossible. Accordingly, the HIV field developed a number of in vitro models to recapitulate many of the properties of latency. One model of HIV latency uses CCL19, which is the ligand of CCR7, to polarize cells towards a resting memory and thus a latency resembling phenotype. Pretreatment of resting $CD4^+$ T cells from blood with CCL19 allows for efficient HIV-1 entry and viral integration with restricted spontaneous viral expression yet robust HIV expression post stimulation consistent with postintegration HIV-1 latency (Saleh et al., *Blood*, 110:4161-4164 (2007)).

ART drugs do not treat latently HIV infected cells. The only drugs that act on these latently HIV infected cells are latency reversing agents (LRAs), but LRAs do not cause latently HIV infected cells to die. Thus, the number of latently HIV infected cells can remain stable over time.

Figure 2:
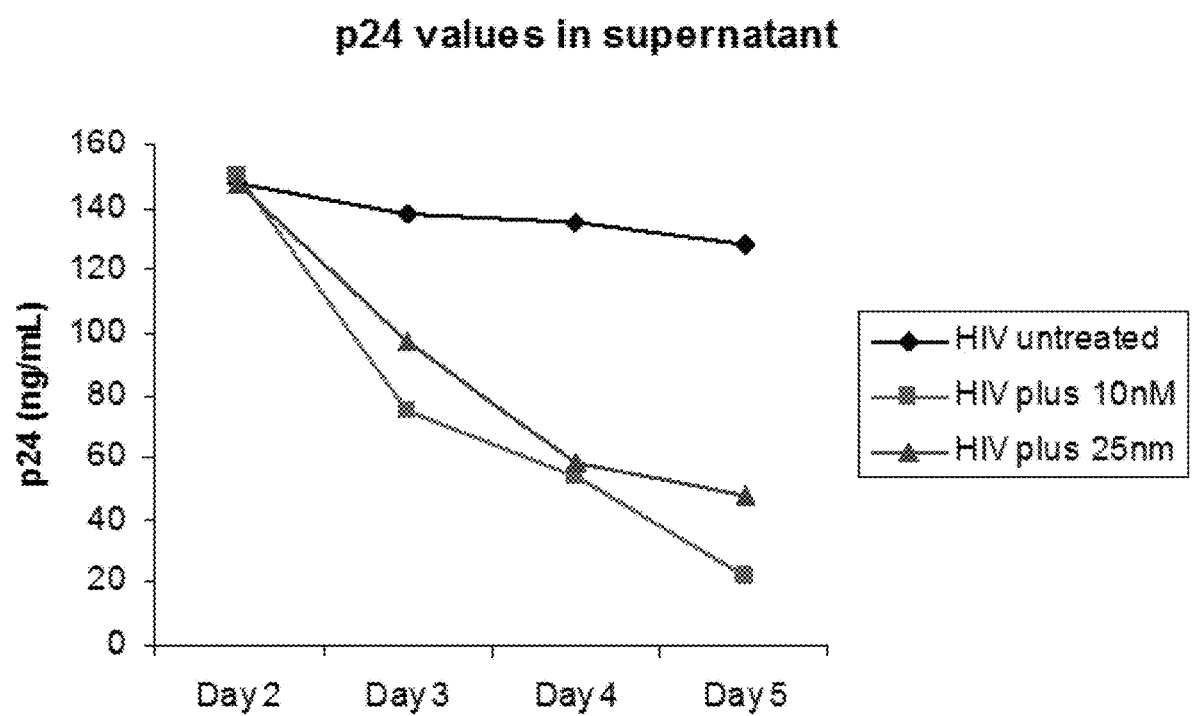
FIG. 2 is a graph plotting the level of p24 (ng/mL) in the supernatant of a culture of HIV IIIb infected Jurkat T cells that were untreated or treated (10 or 25 nM of bortezomib) as described in FIG. 1.
Figure 3:
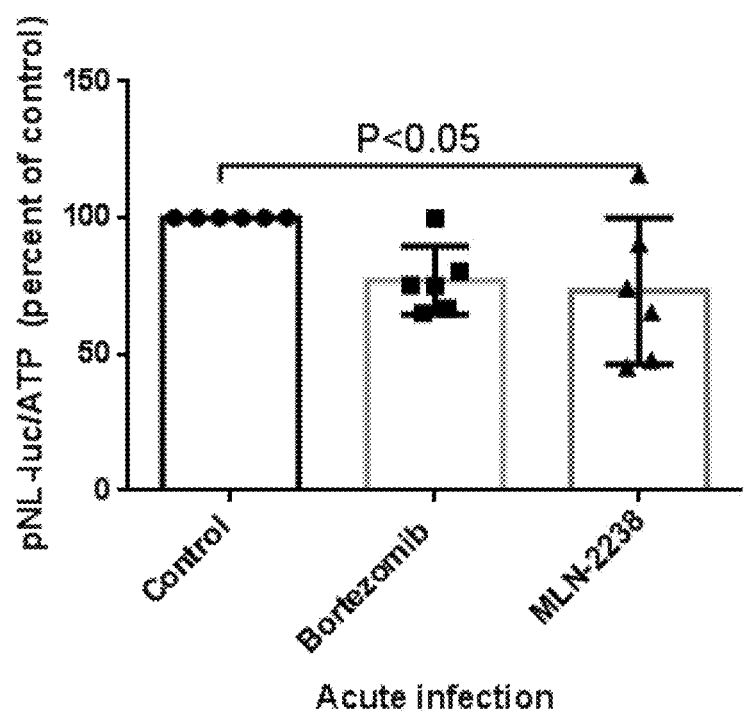
FIGS. 3 and 4. CD4 T cells infected with HIV-pNL4.3-Luc were activated and cultured for three days. Cells were treated with TDF/T20 and then with bortezomib (10 nM) or MLN-2238 (100 nM) or control. Cells were harvested 48 hours after treatment and analyzed for intracellular luciferase (FIG. 3) or proviral DNA (FIG. 4).
Figure 4:
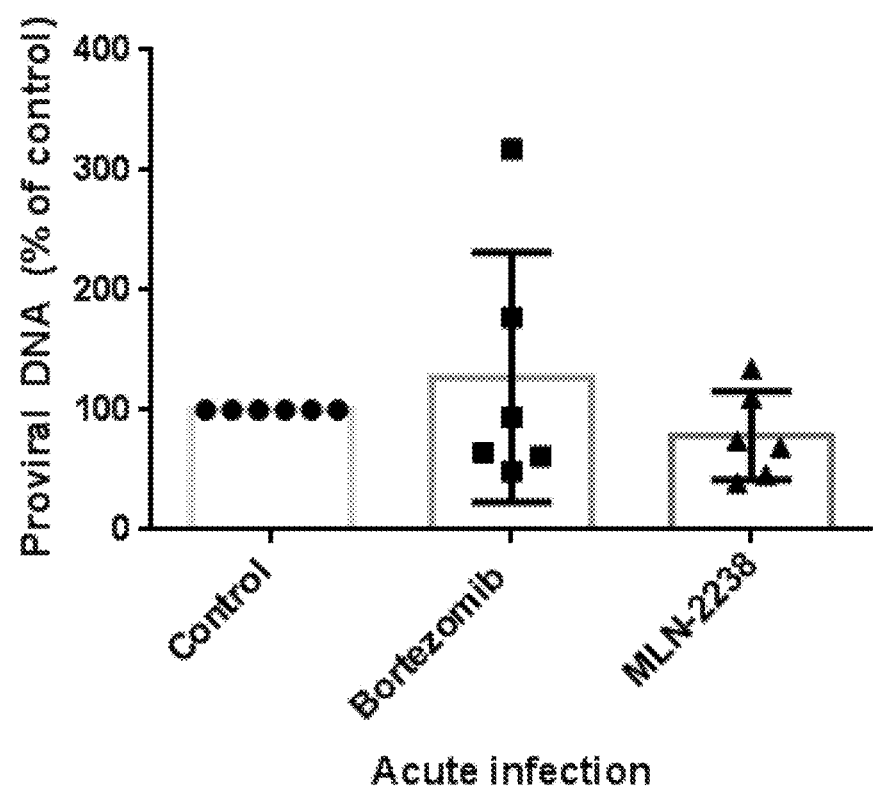
Figure 5:
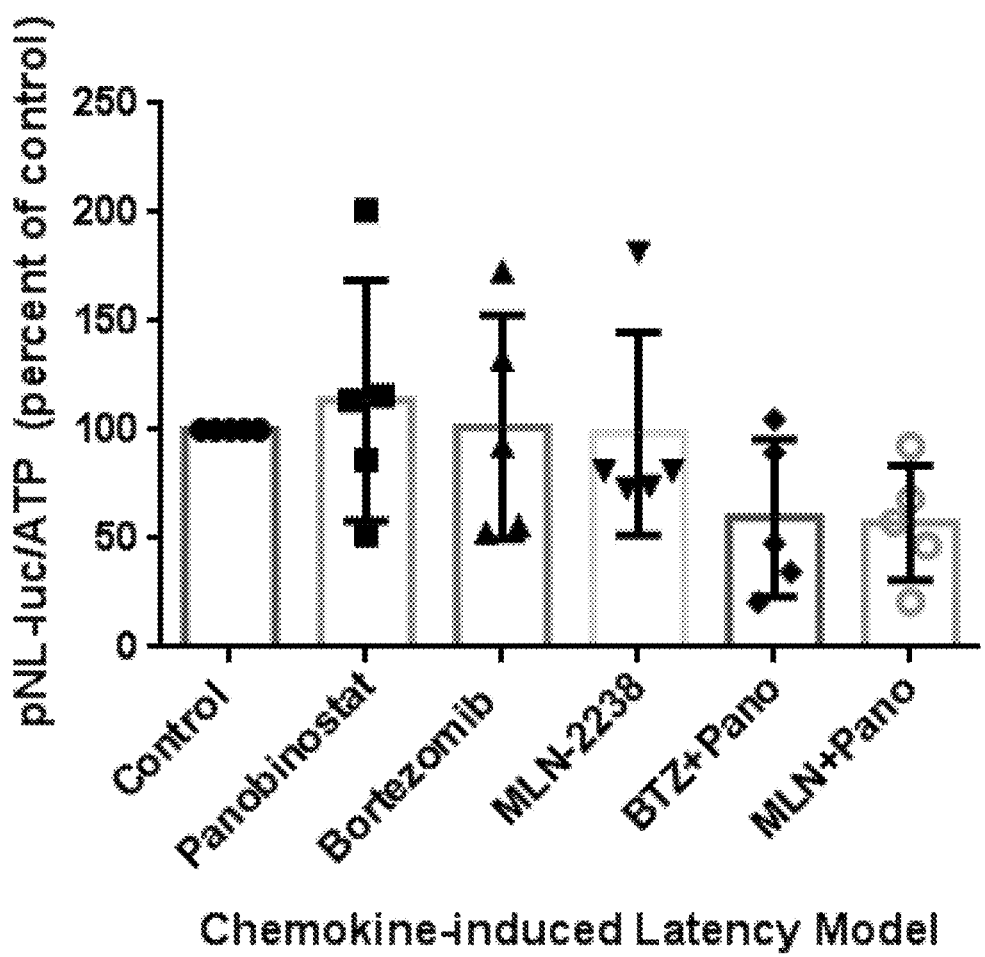
FIG. 5 is a graph plotting resting CD4 T cells treated with CCL19/IL2, infected with HIV-pNL4.3-Luc, and cultured in the presence of TDF/T20. The cells were treated with bortezomib (10 nM) or MLN-2238 (100 nM) or control for 24 hours prior to reactivation with panobinostat. Cells were harvested 48 hours after reactivation and analyzed for intracellular luciferase activity.
Figure 6:
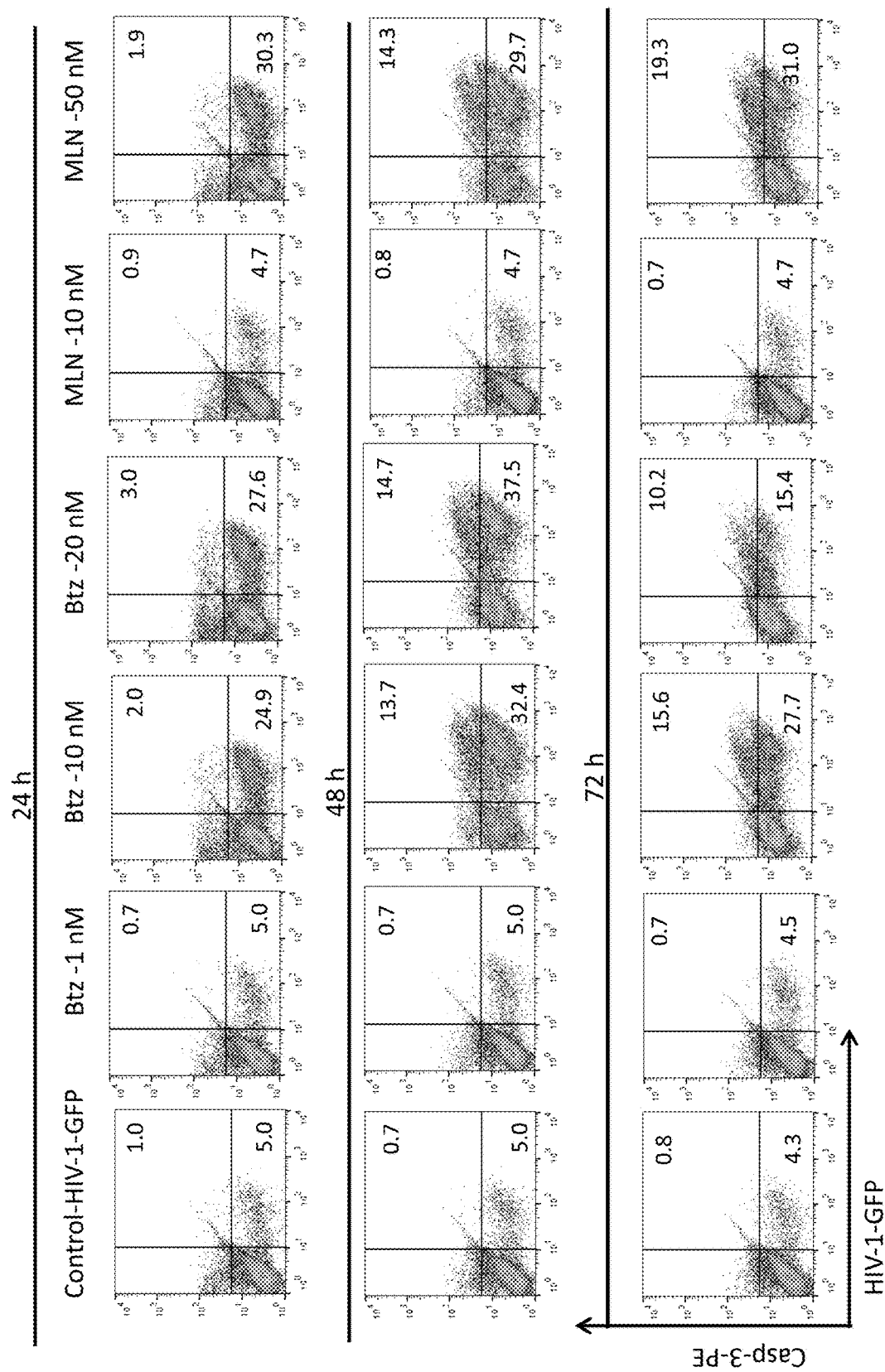
FIG. 6 contains flow cytometry results of J-Lat cells (a model of HIV latency, using GFP tagged HIV) treated with nothing, bortezomib (1, 10, or 20 nM), or MLN-2238 (ixazomib; 10 or 50 nM) and analyzed 24 hours later for activated caspase 3 expression and for HIV expression. Both bortezomib, and ixazomib independently caused HIV reactivation as indicated by increased HIV GFP expression, and caused HIV GFP positive cells to die, as indicated by activated caspase 3 expression in the GFP positive cells.
Figure 7:
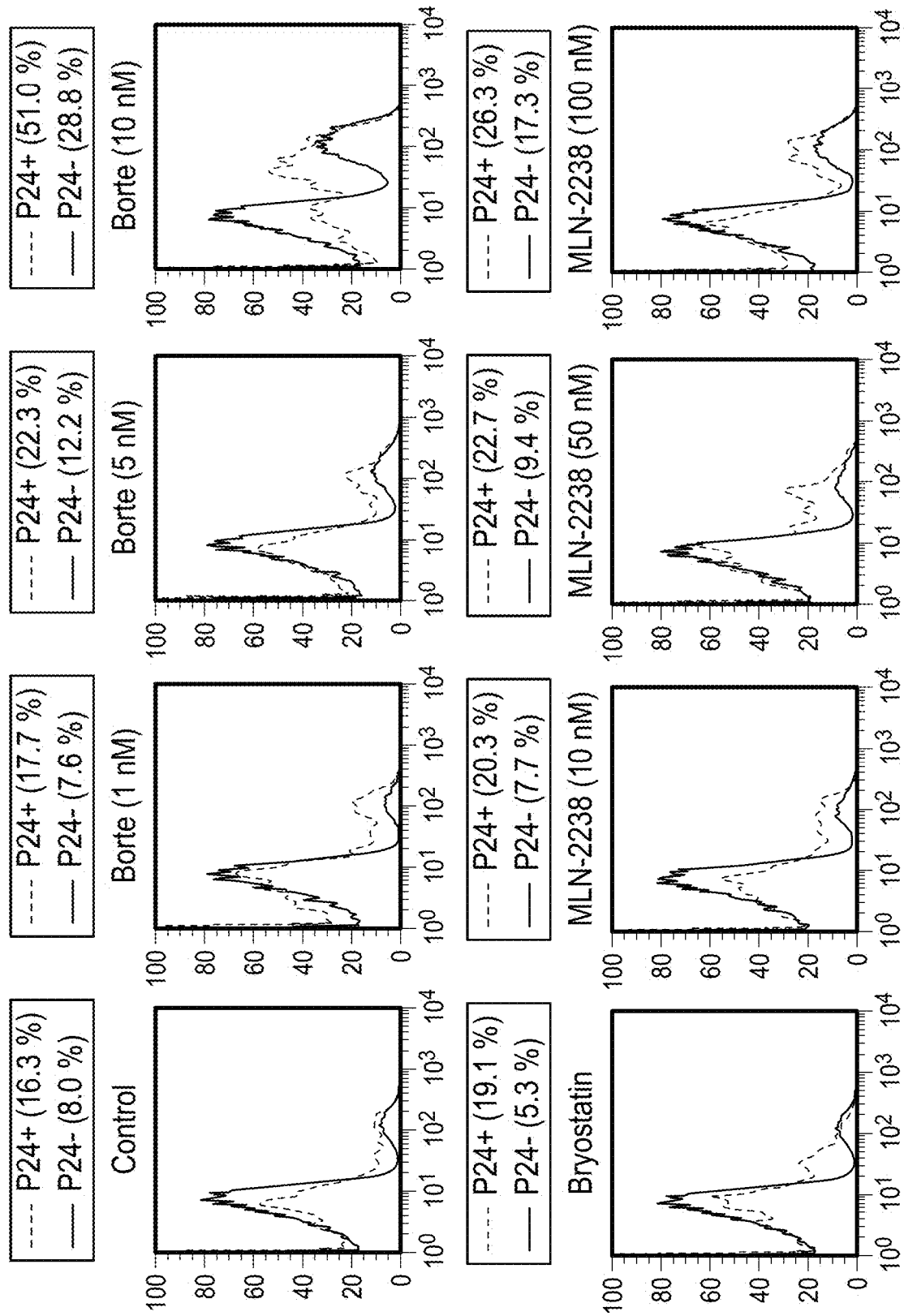
FIG. 7 contains flow cytometry results of CD4 T cells from an HIV positive patient with ART suppressed HIV replication. Cells were treated with bortezomib or MLN-2238 (ixazomib) at the indicated doses and analyzed 48 hours later for intracellular p24 expression (as a measure of HIV reactivation), and for activated caspase 3 expression (as a measure of cell death). Both bortezomib, and ixazomib independently caused HIV reactivation as indicated by increased HIV p24 expression, and caused HIV positive cells to die as indicated by activated caspase 3 expression in the p24 positive cells.
Figure 8:
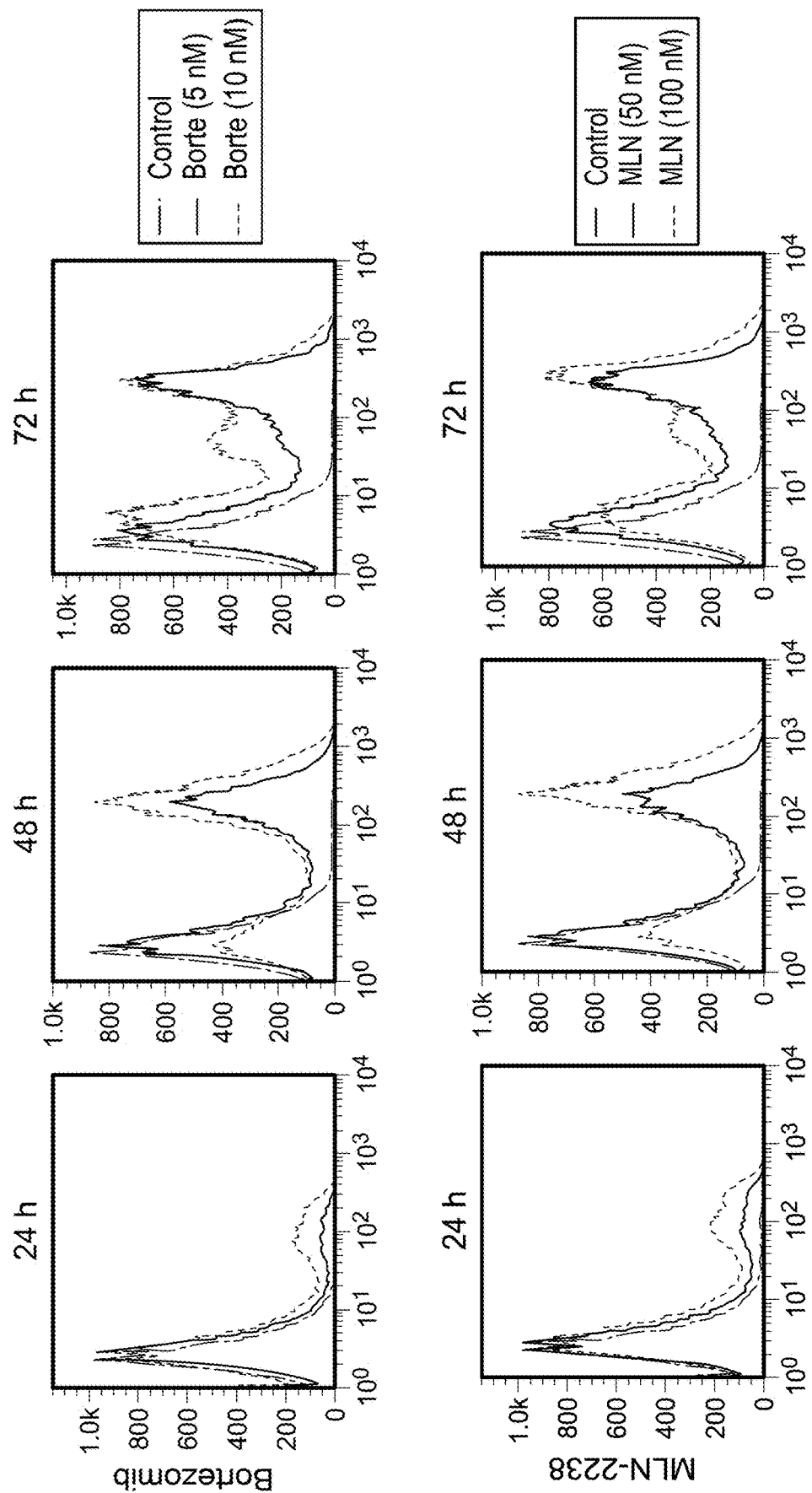
FIG. 8 contains flow cytometry results demonstrating that inhibited budding leads to accumulation of HIV proteins. J-Lat cells (a model of HIV latency using GFP HIV) were treated with bortezomib or ixazomib at the indicated doses and analyzed at 24, 48, and 72 hours. Both drugs caused HIV reactivation from latency.
Figure 9:
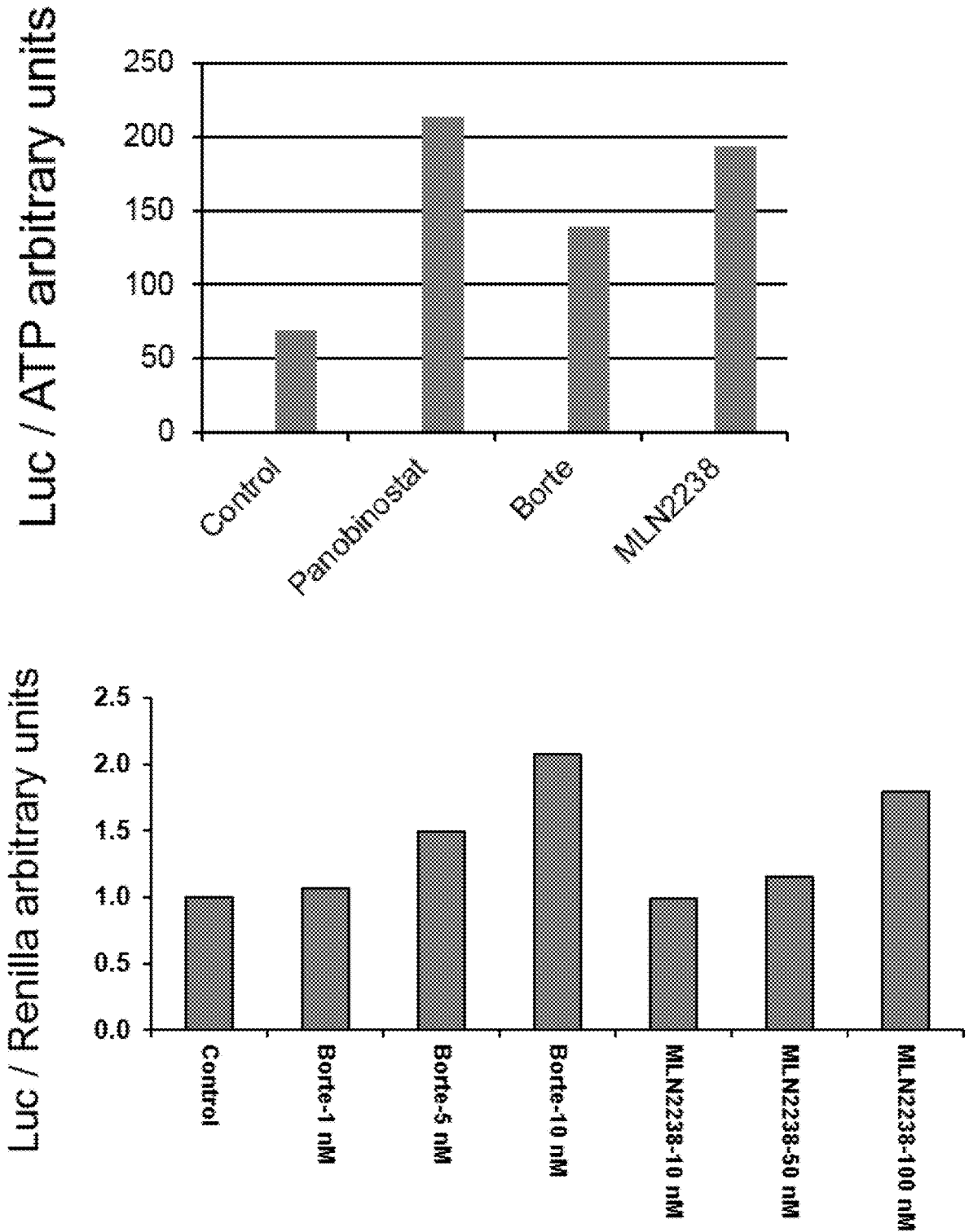
FIG. 9 provides data demonstrating that proteosome inhibitors stimulate HIV. Primary CD4 T cells infected with HIV luc (top panel) or primary CD4 T cells transfected with HIV-LTR Luc and co-transfected TK renilla (bottom panel) were treated with the indicated doses of bortezomib or ixazomib, and analyzed for Luc expression as a measure of HIV reactivation. Both drugs independently reactivated HIV in primary CD4 T cell model systems.
Figure 10:
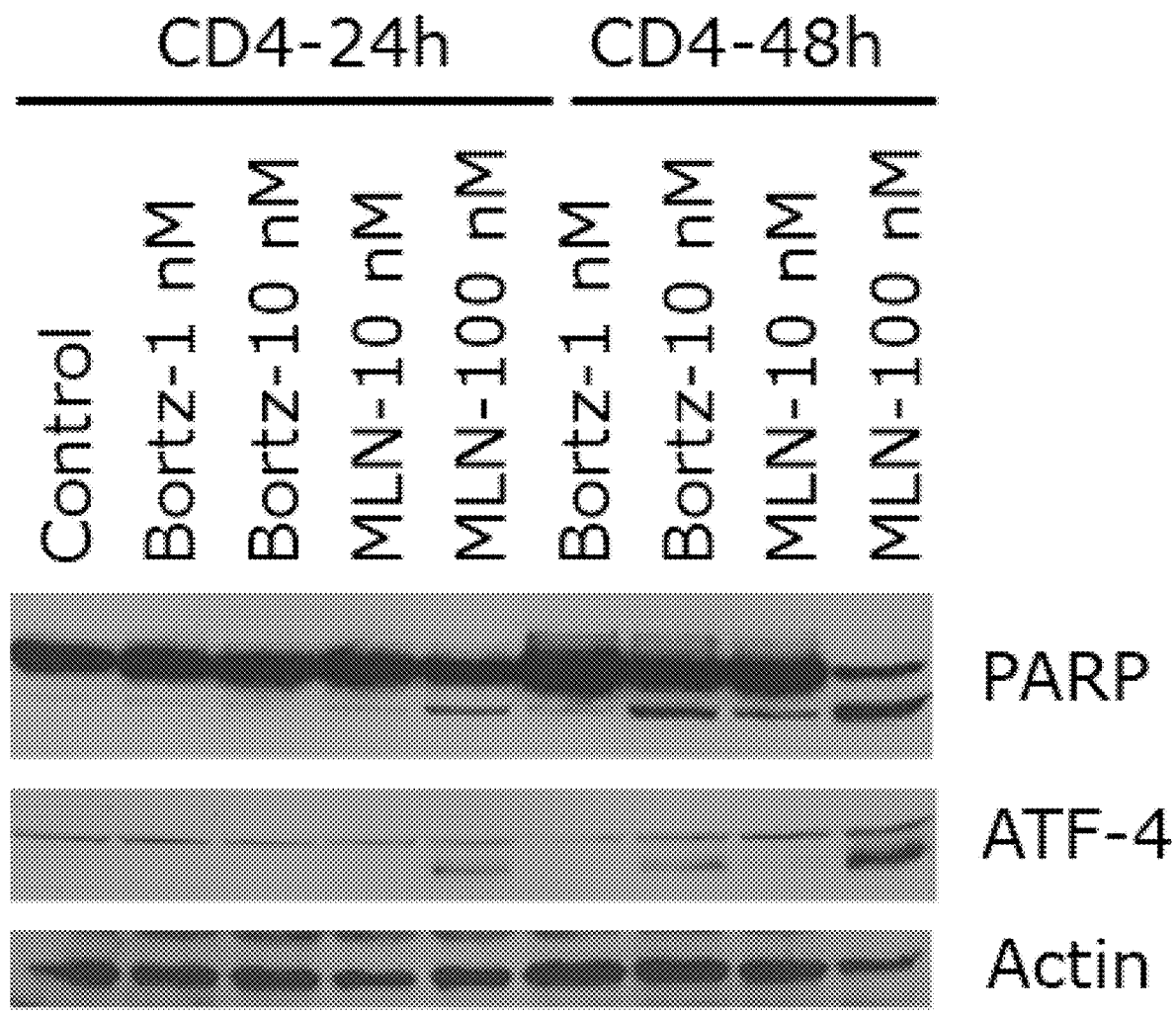
FIG. 10 provides data demonstrating that proteosome inhibitors stimulate ATF4, leading to HIV-LTR activation. Proteosome inhibitors activated the unfolded protein response (UPR) pathway, which includes ATF-4, and ATF4 can independently activate the HIV LTR. To determine if AFT4 is a plausible mechanism of HIV reactivation in primary CD4 T cells, cells were treated with bortezomib or ixazomib, and ATF-4 was analyzed over time.
Figure 11:
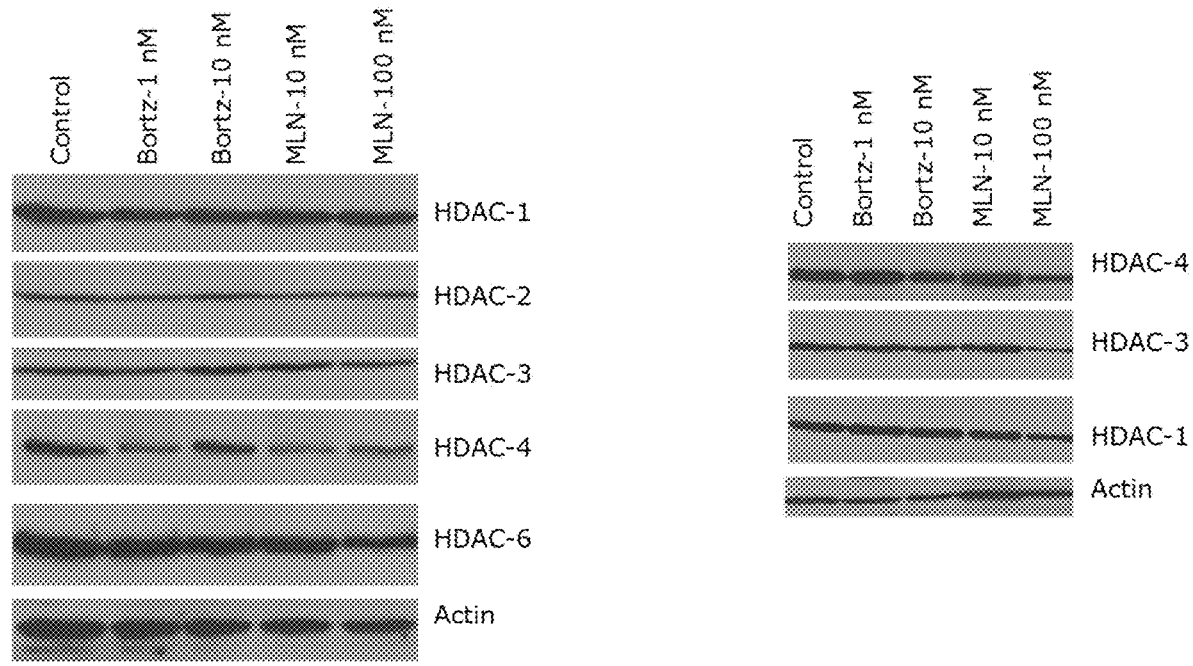
FIG. 11. HIV latency is maintained in part by the action of HDAC, and HDAC inhibitors caused HIV reactivation. Proteosome inhibitors were analyzed for the ability to alter the expression of HDAC. Bortezomib and ixazomib decreased HDAC-1, HDAC-3, and HDAC-4 expression in primary CD4 T cells.
Figure 12:
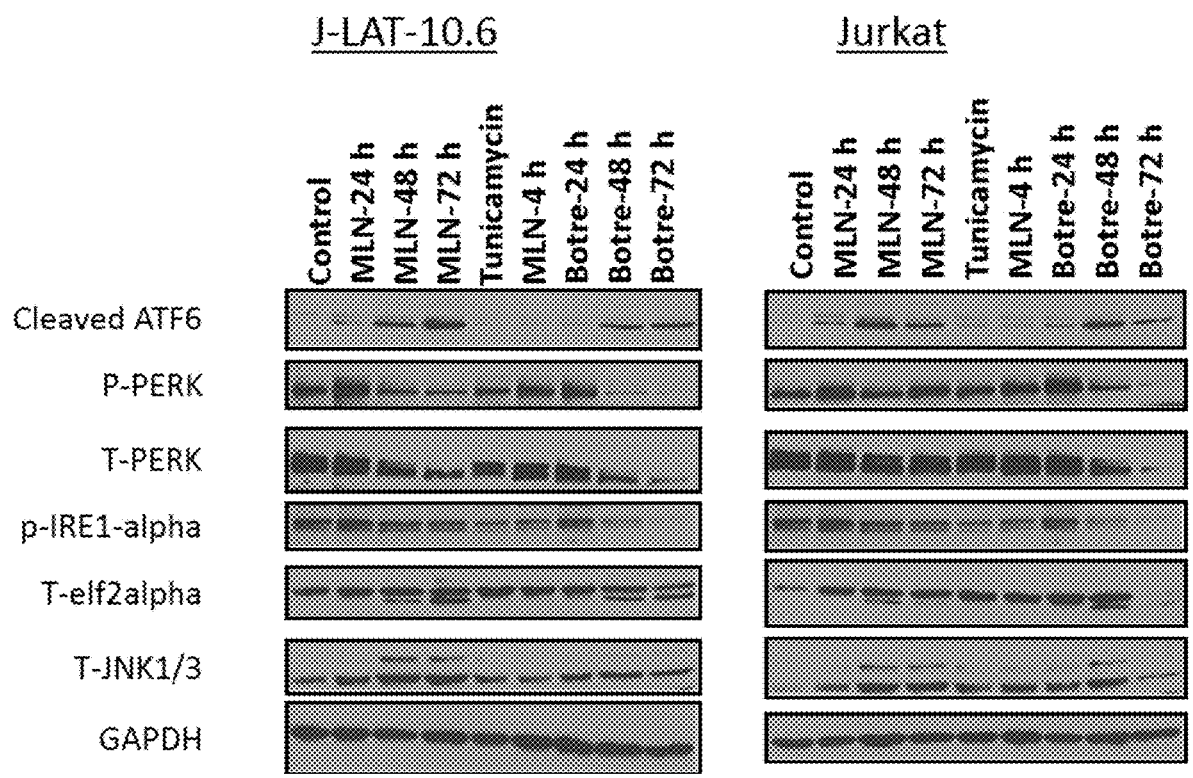
FIG. 12. J-LAT-10.6 or Jurkat cells were treated with bortezomib (10 nM) or ixazomib (50 nM) for the indicated times. Bortezomib and ixazomib induced phospho PERK, phospho IRE1, and JNK activation in J Lat cells, indicating the activation of the UPR pathway.
Figure 13:
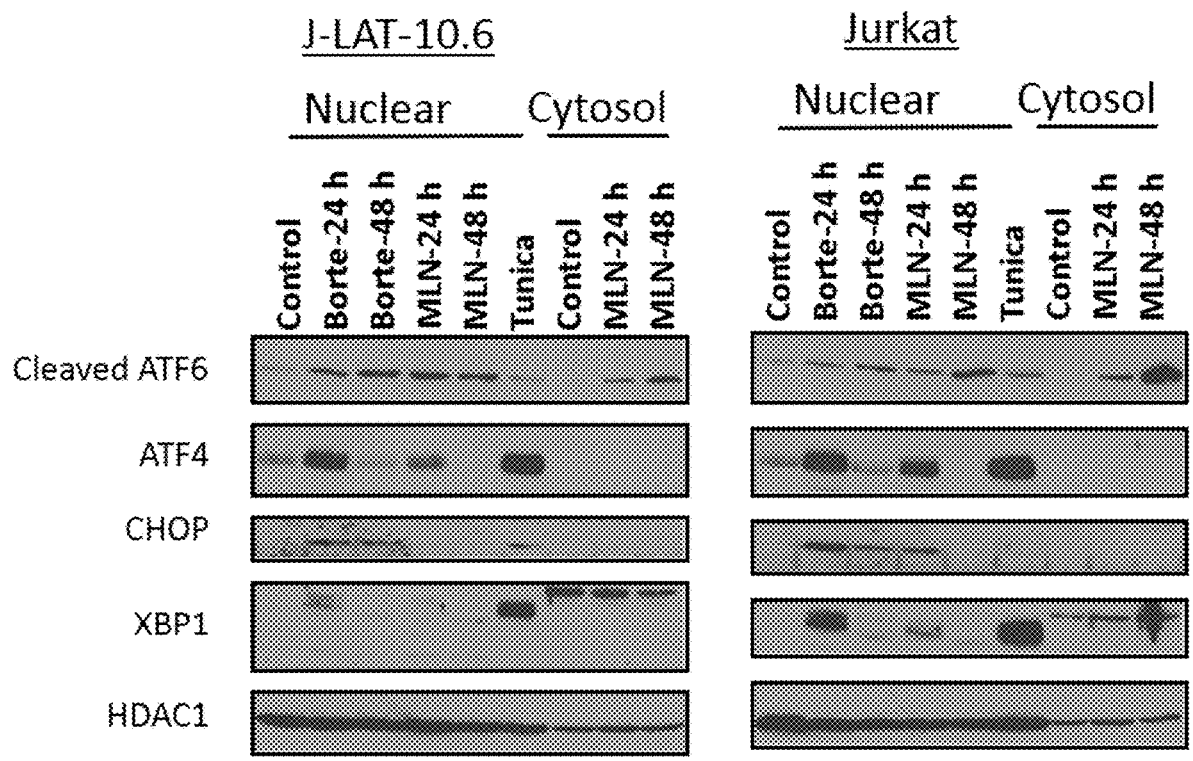
FIG. 13. J-LAT-10.6 or Jurkat cells were treated with bortezomib (10 nM) or ixazomib (50 nM) for the indicated times. Bortezomib and ixazomib induced ATF4 and CHOP translocation into the nucleus, and ATF6 cleavage in J Lat cells, indicating the activation of the UPR pathway.

The results provided herein (see, e.g., FIGS. 1-13) demonstrate that proteosome inhibitors alone such as bortezomib or ixazomib can induce HIV reactivation and that, following HIV reactivation, HIV proteins accumulate in the HIV infected cell. Moreover, the results provided herein demonstrate that when HIV is reactivated in latently HIV infected cells (whether the HIV reactivation is induced by a proteosome inhibitor, another agent such as an LRA, or a condition such as an inflammatory reaction) in the presence of a proteosome inhibitor, those HIV reactivating cells die, resulting in fewer cells containing HIV.

Example 2

Reducing the Number of Latently HIV Infected Cells within an HIV Infected Human

A human having an HIV infection is treated with an ART regimen that includes 400 mg po bid of Raltegravir or 50 mg per day of Dolutegravir plus either two nucleoside analogues such as tenofovir (300 mg per day) and emtracitibine (200 mg per day or Complera® (emtricitabine, rilpivirine, and tenofovir; fixed dose pill once daily). In addition, the human is treated with 2 mg/m² of ixazomib twice a week.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing apoptosis susceptibility of latently HIV infected cells within a human infected with HIV, wherein said method comprises administering ixazomib to said human to contact latently HIV infected cells with 50 nM to 100 nM of said ixazomib, thereby increasing the susceptibility of latently HIV infected cells within said human to pro-apoptotic HIV proteins.

2. The method of claim 1, wherein said infected cells are resting memory CD4$^+$ T cells.

3. The method of claim 1, wherein said method further comprises administering a latency reversing agent to said human to treat HIV.

4. The method of claim 3, wherein said latency reversing agent is selected from the group consisting of an HDAC inhibitor, a phorbol ester, IL-2, and a bromodomain inhibitor.

5. The method of claim 1, wherein said method further comprises administering an immunotherapeutic agent, a vaccine, or a nucleic acid to said human to treat HIV.

6. The method of claim 1, wherein said method further comprises administering an immunotherapeutic agent to said human to treat HIV, wherein said immunotherapeutic agent is IL-15.

7. The method of claim 1, wherein said method further comprises administering a vaccine to said human to treat HIV.

8. The method of claim 1, wherein said method further comprises administering a nucleic acid to said human to treat HIV, wherein said nucleic acid is designed to reduce CCR5 polypeptide expression.

* * * * *